(12) United States Patent
Ito et al.

(10) Patent No.: US 8,642,773 B2
(45) Date of Patent: *Feb. 4, 2014

(54) P38MAP KINASE INHIBITOR

(75) Inventors: Kazuhiro Ito, London (GB); Peter Strong, London (GB); William Garth Rapeport, London (GB); Peter John Murray, London (GB); John King-Underwood, Pendock (GB); Jonathan Gareth Williams, Nottingham (GB); Stuart Onions, Nottingham (GB); Catherine Elisabeth Charron, London (GB)

(73) Assignee: Respivert Ltd., Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/262,266

(22) PCT Filed: Apr. 1, 2010

(86) PCT No.: PCT/GB2010/050575
§ 371 (c)(1),
(2), (4) Date: Dec. 1, 2011

(87) PCT Pub. No.: WO2010/112936
PCT Pub. Date: Oct. 7, 2010

(65) Prior Publication Data
US 2012/0136031 A1    May 31, 2012

Related U.S. Application Data

(60) Provisional application No. 61/166,594, filed on Apr. 3, 2009.

(30) Foreign Application Priority Data

Apr. 6, 2009  (GB) .................................. 0905955.1

(51) Int. Cl.
*A61K 31/44* (2006.01)
*C07D 401/00* (2006.01)

(52) U.S. Cl.
USPC ........................................ 546/268.4; 514/341

(58) Field of Classification Search
None
See application file for complete search history.

(56) References Cited

U.S. PATENT DOCUMENTS

| | | |
|---|---|---|
| 6,492,529 B1 | 12/2002 | Kapadia et al. |
| 6,525,046 B1 | 2/2003 | Cirillo et al. |
| 6,916,814 B2 | 7/2005 | Moss et al. |
| 7,329,670 B1 | 2/2008 | Dumas et al. |
| 7,625,915 B2 | 12/2009 | Dumas et al. |
| 2004/0180906 A1 | 9/2004 | Flynn et al. |
| 2004/0192653 A1 | 9/2004 | Munson et al. |
| 2007/0010529 A1 | 1/2007 | Takahashi et al. |
| 2008/0113967 A1 | 5/2008 | Flynn et al. |
| 2008/0207699 A1 | 8/2008 | Hoelzemann et al. |
| 2008/0300281 A1 | 12/2008 | Dumas et al. |
| 2009/0074676 A1 | 3/2009 | Yang |
| 2010/0104536 A1 | 4/2010 | Modi et al. |
| 2011/0212962 A1 | 9/2011 | Ito et al. |
| 2011/0269800 A1 | 11/2011 | Ito et al. |
| 2011/0294812 A1 | 12/2011 | Ito et al. |
| 2011/0312963 A1 | 12/2011 | Ito et al. |

FOREIGN PATENT DOCUMENTS

| | | |
|---|---|---|
| WO | WO 99-23091 | 5/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/47529 | 9/1999 |
| WO | WO 00/43384 | 7/2000 |
| WO | WO 01/04115 | 1/2001 |
| WO | WO 02/066442 | 8/2002 |
| WO | WO 02/092576 | 11/2002 |
| WO | WO 03/005999 | 1/2003 |
| WO | WO 03/068223 | 8/2003 |
| WO | WO 03/068228 | 8/2003 |

(Continued)

OTHER PUBLICATIONS

Pargellis, et al., "Inhibition of P38 MAP Kinase by Utilizing a Novel Allosteric Binding Site", Nature Structural Biology, Apr. 1, 2002; pp. 268-272; vol. 9, No. 4.
ISR PCT/GB2010/050575, Dated Jun. 30, 2010 (RSP-5004USPCT3).

(Continued)

*Primary Examiner* — Janet L Andres
*Assistant Examiner* — Heidi Reese
(74) *Attorney, Agent, or Firm* — Mary Appollina; Samuel M. Kais

(57) ABSTRACT

The present invention relates to a compound of formula (I):

(1)

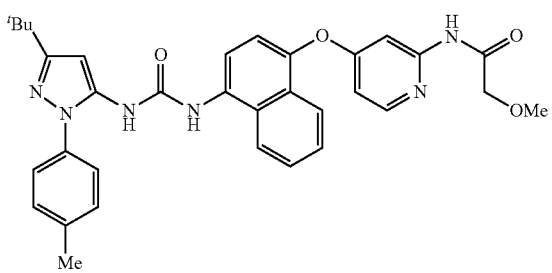

or a pharmaceutically acceptable salt thereof, including all stereoisomers and tautomers, which is an inhibitor of p38 mitogen-activated protein kinase enzymes (referred to herein as p38 MAP kinase inhibitors), particularly the alpha and gamma kinase sub-types thereof, and its use in therapy, including in pharmaceutical combinations, especially in the treatment of inflammatory diseases, including inflammatory diseases of the lung, such as COPD.

4 Claims, 3 Drawing Sheets

(56) References Cited

FOREIGN PATENT DOCUMENTS

| WO | WO 03/072569 | 9/2003 |
|---|---|---|
| WO | WO 03/084503 | 10/2003 |
| WO | WO 2004/004720 | 1/2004 |
| WO | WO 2004/014387 | 2/2004 |
| WO | WO 2004/021988 | 3/2004 |
| WO | WO 2004/060306 | 7/2004 |
| WO | WO 2004/078746 | 9/2004 |
| WO | WO 2004/089929 | 10/2004 |
| WO | WO 2004/100946 | 11/2004 |
| WO | WO 2005/002673 | 1/2005 |
| WO | WO 2005/018624 | 3/2005 |
| WO | WO 2005/048948 | 6/2005 |
| WO | WO 2005/110994 | 11/2005 |
| WO | WO 2005/113511 | 12/2005 |
| WO | WO 2006/009741 | 1/2006 |
| WO | WO 2006/014290 | 2/2006 |
| WO | WO 2006/015775 | 2/2006 |
| WO | WO 2006/028524 | 3/2006 |
| WO | WO 2006/043090 | 4/2006 |
| WO | WO 2006/062984 | 6/2006 |
| WO | WO 2006/068591 | 6/2006 |
| WO | WO 2006/072589 | 7/2006 |
| WO | WO 2006/081034 | 8/2006 |
| WO | WO 2006/105844 | 10/2006 |
| WO | WO 2007/002635 | 1/2007 |
| WO | WO 2007/017083 | 2/2007 |
| WO | WO 2007/038425 | 4/2007 |
| WO | WO 2007/059202 | 5/2007 |
| WO | WO 2007/064872 | 6/2007 |
| WO | WO 2008/016192 | 2/2008 |

OTHER PUBLICATIONS

Dumas et al., "Synthesis and Pharmacological Characterization of a Potent, Orally Active p38 Kinase Inhibitor", Bioorganic & Medicinal Chemistry Letters 12 (2002) 1559-1562.

Regan et al., "Structure-Activity Relationships of the p38α MAP Kinase Inhibitor 1-(5-*tert*-Butyl-2-*p*-toly1-2*H*-pyrazol-3-yl)-3-[4-(2-morpholin-4-yl-ethoxy)naphthalen-1-yl]urea (BIRB 796)", Journal of Medicinal Chemistry 46 (2003) 4676-4686.

Friedenreich, et al., "State of the epidemiological Evidence on Physical Activity and Cancer Prevention", European Journal of Cancer, vol. 46, 2010, pp. 2593-2604.

ISR PCT/GB2009/051703, Dated Apr. 15, 2010.
ISR PCT/GB2009/051702, Dated Jun. 23, 2011.
ISR PCT/GB2009/051304, Dated Apr. 14, 2011.
ISR PCT/GB2009/051303, Dated Apr. 14, 2011.

Figure 1: Neutrophil accumulation in BALF (Compound (1))
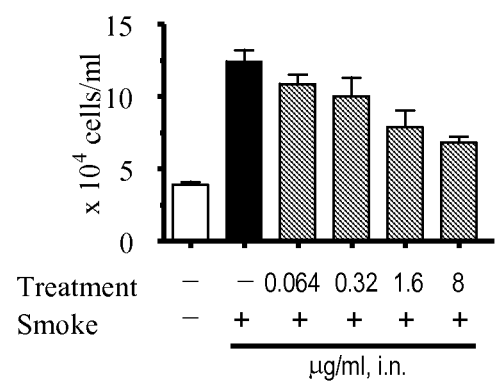
Figure 2: MOMA2⁺ Macrophage accumulation in BALF (Compound (1))
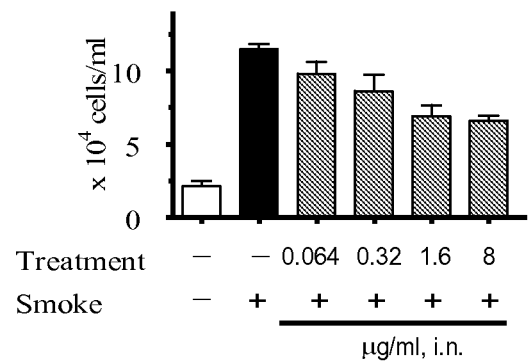

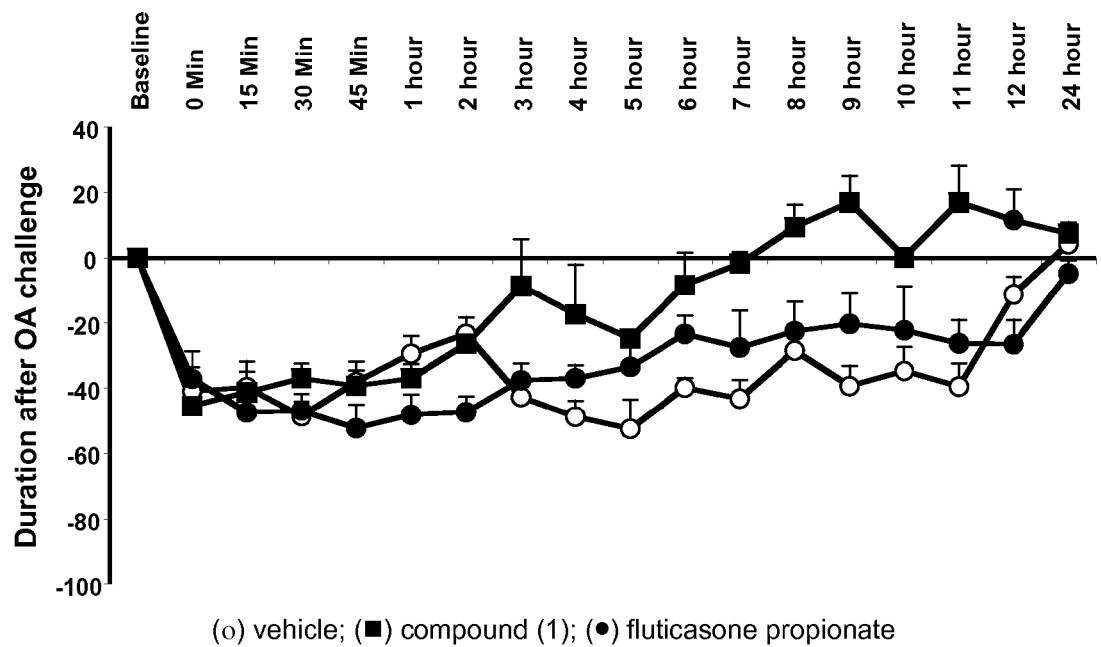
Figure 3: Change of sGaw values after OVA exposure in OVA sensitized PIV3 infected guinea pigs (Compound (1))
(o) vehicle; (■) compound (1); (●) fluticasone propionate

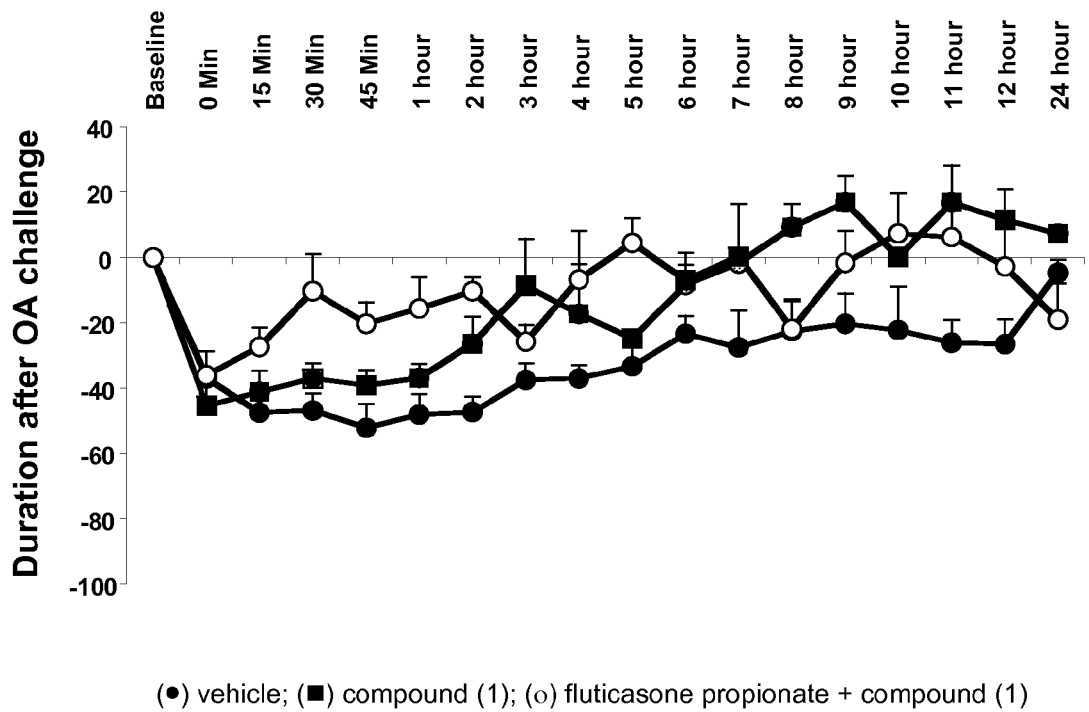
Figure 4: Change of sGaw values after OVA exposure in OVA sensitized PIV3 infected guinea pigs (Compound (1))
(●) vehicle; (■) compound (1); (o) fluticasone propionate + compound (1)

P38 MAP KINASE INHIBITOR

This application is a National Stage application under 35 U.S.C. 371 of PCT International Application No. PCT/GB2010/050575, filed Apr. 1, 2010, which claims priority from Patent Application No. GB 0905955.1, filed Apr. 6, 2009, the contents of which are hereby incorporated by reference.

FIELD OF THE INVENTION

The invention relates to a compound which is an inhibitor of p38 mitogen-activated protein kinase enzymes (referred to herein as p38 MAP kinase inhibitors), particularly the alpha and gamma kinase sub-types thereof, and its use in therapy, including in pharmaceutical combinations, especially in the treatment of inflammatory diseases, including inflammatory diseases of the lung, such as COPD.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages (Smith, S. J. (2006) *Br. J. Pharmacol.* 149:393-404) and detectable in neutrophils, CD4+ T cells and endothelial cells (www.genecard.org, Karin, K. (1999) *J. Immunol.*). Very little is known about the expression of p38 MAPK gamma but it is expressed more in brain, skeletal muscle and heart, as well as in lymphocytes and macrophages (www.genecard.org).

Selective small molecule inhibitors of p38 MAPK-gamma and -delta are not currently available, but one existing compound, BIRB 796, is known to have pan-isoform inhibitory activity. The p38 gamma and p38 delta inhibition is observed at higher concentrations of the compound than those required to inhibit p38 MAPK alpha (Kuma, Y. (2005) *J. Biol. Chem.* 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, severe asthma and COPD. There is now abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith, S. J. (2006) *Br. J. Pharmacol.* 149:393-404 describes the inhibitory effect of p38 MAP kinase inhibitors on TNFα (but not IL-8) release from human PBMCs. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues obtained from patients with COPD, who are generally corticosteroid insensitive, (Smith, S. J. (2006) *Br. J. Pharmacol.* 149:393-404) and in vivo animal models (Underwood, D. C. et al. (2000) 279:895-902; Nath, P. et al. (2006) *Eur. J. Pharmacol.* 544:160-167; Medicherla S. et al. (2008) *J. Pharm. Exp. Ther.* 324:921-929). Irusen and colleagues also suggested the possibility of involvement of p38 MAPK α/β on corticosteroid insensitivity via reduction of binding affinity of glucocorticoid receptor (GR) in nuclei (Irusen, E. et al., (2002) *J. Allergy Clin. Immunol.,* 109:649-657). Clinical experience with a range of p38 MAP kinase inhibitors, including AMG548, BIRB 796, VX702, SCIO469 and SCIO323 is described in Lee et al. (2005) *Current Med. Chem.* 12:2979-2994.

COPD is a condition in which the underlying inflammation has been reported to be substantially resistant to the anti-inflammatory effects of inhaled corticosteroids. Consequently, an effective strategy for treating COPD may well be to develop an intervention which both has inherent anti-inflammatory effects and is able to increase the sensitivity of lung tissues from COPD patients to inhaled corticosteroids. The recent publication of Mercado et al. (2007) *American Thoracic Society Abstract A*56) demonstrates that silencing p38 gamma has the potential to restore sensitivity to corticosteroids. Thus there may be a "two pronged" benefit to the use of a p38 MAP kinase inhibitor for the treatment of COPD and severe asthma.

There is now a substantial body of evidence which strongly implicates the role of respiratory viral infections in initiating exacerbations in patients suffering from asthma and/or COPD. Exacerbations require an increase in treatment intensity to re-establish control of disease symptomology. If severe, exacerbations may well result in the hospitalisation or, at its most extreme, the death of patients. Those viruses which are commonly associated with exacerbations include rhinovirus, influenza and respiratory syncitial virus. The cellular responses to these viruses are now known to include the up-regulation of ICAM1 (intercellular adhesion molecule 1) and release of cytokines, as well as the replication of virus particles. There has been some investigation into the effect of p38 MAP kinase inhibitors on these viral responses and some reports suggest that protective effects can be detected with p38 MAP kinase inhibitors. In particular, some reports suggest that inhibition of virus-induced release of IL-8 can be achieved in vitro with the known compound, SB203580. It is noteworthy that the assessment of an agent's efficacy to reduce rhinovirus-induced inflammation and virus replication in preclinical in vivo models remains a significant challenge. However, there are well-established in vivo models of influenza in the mouse and parainfluenza in the guinea pig.

The major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specially mentioned above.

There remains a need to identify and develop new compounds therapeutically useful as p38 MAP kinase inhibitors which have improved therapeutic potential, in particular which are more efficacious, longer acting and/or less toxic at the relevant therapeutic dose. An objective of the present invention is to provide a compound which inhibits p38 MAP kinase, for example with certain sub-type specificity, which shows good anti-inflammatory potential.

SUMMARY OF THE INVENTION

According to the invention, there is provided a compound of formula (1)

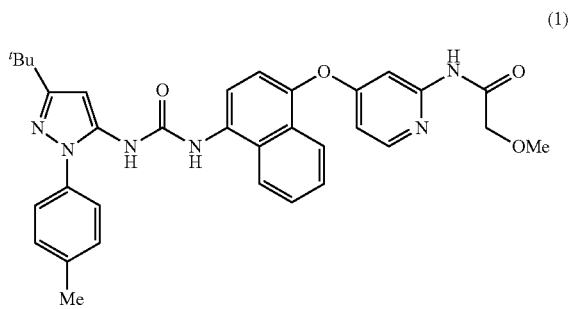 [SMILES: COCC(=O)Nc1cc(Oc2ccc(NC(=O)Nc3cc(C(C)(C)C)nn3-c3ccc(C)cc3)c3ccccc23)ccn1]

(1)

or a pharmaceutically acceptable salt or solvate thereof, including all stereoisomers and tautomers thereof.

The systematic name of the compound of formula (1) is N-(4-(4-(3-(3-tert-Butyl-1-p-tolyl-1H-pyrazol-5-yl)ureido)naphthalen-1-yloxy)pyridin-2-yl)-2-methoxyacetamide.

DETAILED DESCRIPTION OF THE INVENTION

Examples of salts of compound (1) include all pharmaceutically acceptable salts, such as, without limitation, acid addition salts of strong mineral acids such as HCl and HBr salts and addition salts of strong organic acids such as a methansulfonic acid salt.

As employed herein below the definition of a compound of formula (1) is intended to include salts, solvates, and all tautomers of said compound, unless the context specifically indicates otherwise. Examples of solvates include hydrates.

The invention provided herein extends to prodrugs of the compound of formula (1), that is to say compounds which break down and/or are metabolised in vivo to provide an active compound of formula (1). General examples of prodrugs include simple esters, and other esters such as mixed carbonate esters, carbamates, glycosides, ethers, acetals and ketals.

In a further aspect of the invention there is provided one or more metabolites of the compound of formula (1), in particular a metabolite that retains one or more of the therapeutic activities of the compound of formula (1). A metabolite, as employed herein, is a compound that is produced in vivo from the metabolism of the compound of formula (1), such as, without limitation, oxidative metabolites and/or metabolites generated, for example, from O-dealkylation.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The disclosure also extends to all polymorphic forms of the compounds herein defined.

An example of a route of preparing the compound of formula (1) is shown below in scheme 1:

Scheme 1

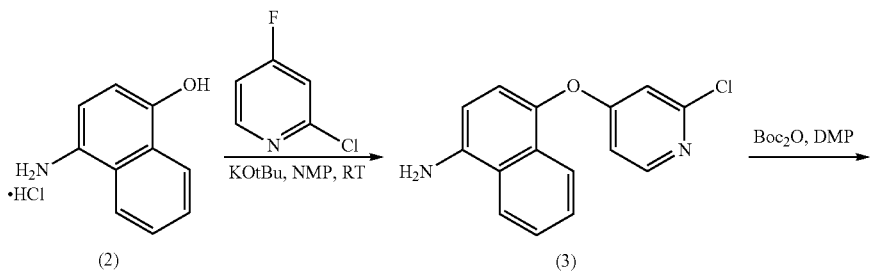

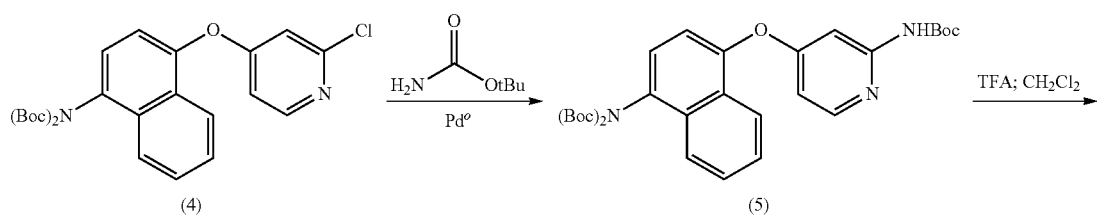

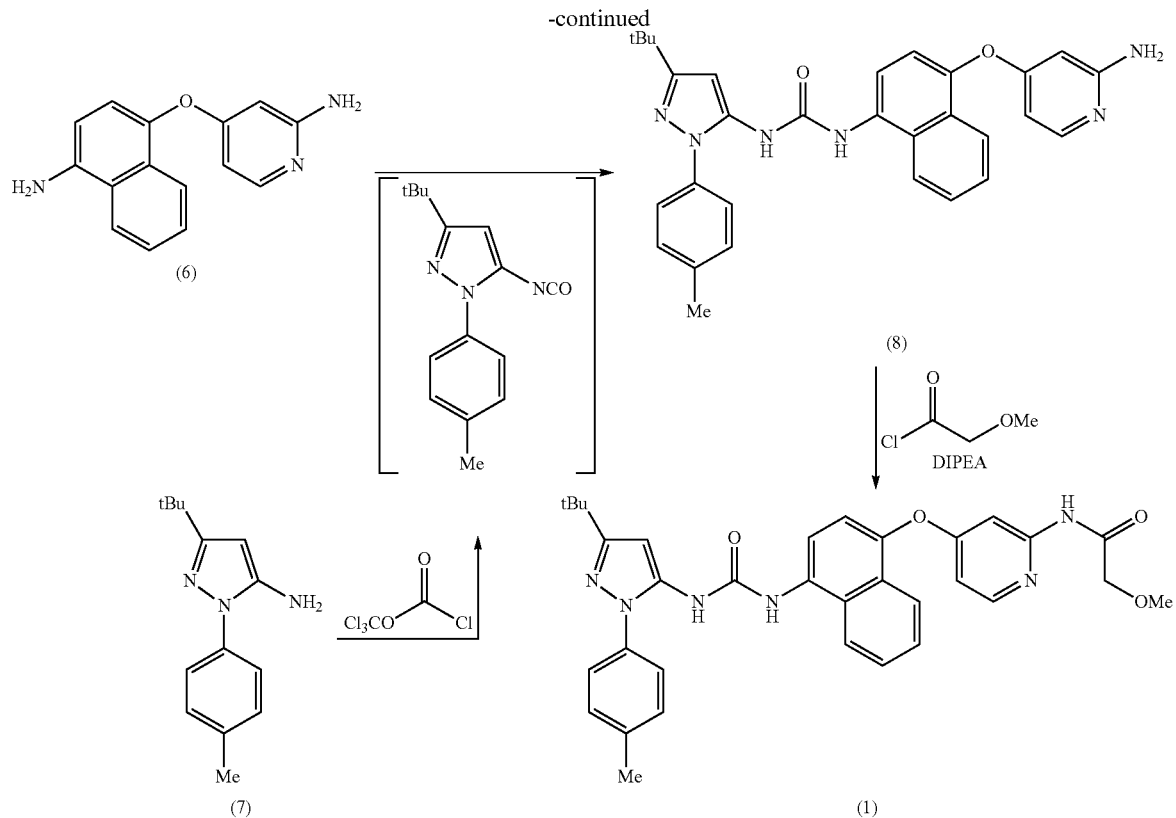

Thus the compound of formula (1) can be prepared by a process comprising reacting a compound of formula (8):

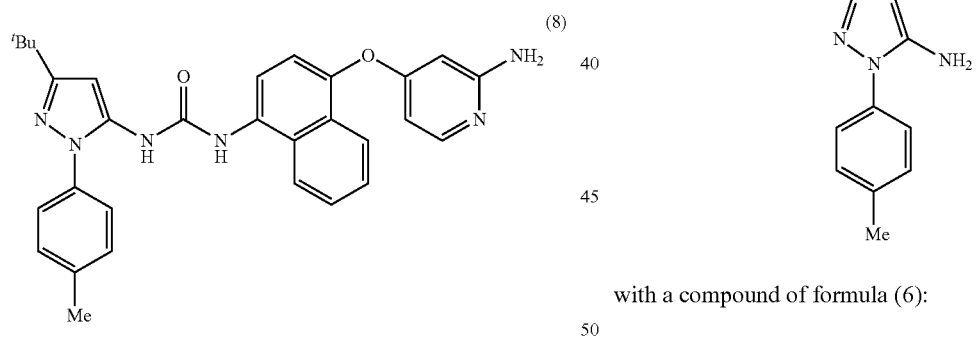

with a compound of formula (A):

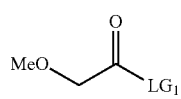

where $LG_1$ is a leaving group for example halogen, such as chloro.

The reaction is suitably carried out in the presence of a base (e.g. N,N-diisopropylethylamine).

Compounds of formula (8) can be prepared by reacting a compound of formula (7)

(7)

with a compound of formula (6):

(6)

and a compound of formula (B):

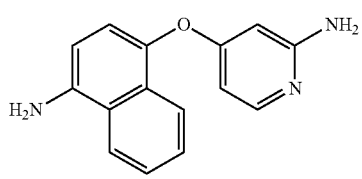

wherein LG$_2$ and LG$_3$ each independently represent leaving groups (e.g. LG$_2$ is Cl$_3$CO— and LG$_3$ is Cl. Alternatively both LG$_2$ and LG$_3$ may be the same, for example LG$_2$ and LG$_3$ both represent imidazolyl or halogen such as chloro).

The reaction is suitably carried out in an aprotic solvent (e.g. dichloromethane), using appropriate protecting groups for chemically sensitive groups.

A compound of formula (6) may be prepared by reaction of a compound of formula (4a):

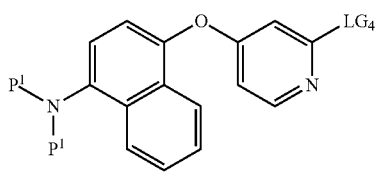
(4a)

wherein P$^1$ is a suitable amine protective group and LG$_4$ represents a leaving group such as chloro, with a compound of formula (C)

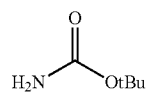
(C)

for example in the presence of a suitable catalyst such as a homogeneous palladium catalyst, followed by removal of the amine protective groups. For example, when the protective groups are tert-butoxycarbonyl, their removal can be achieved by treatment with TFA in dichloromethane.

Compounds of formula (4a) may be prepared by protecting a compound of formula (3a):

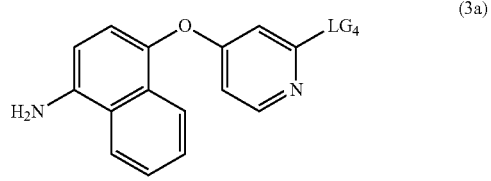
(3a)

for example employing di-tert-butyl dicarbonate and DMAP, wherein LG$_4$ represents a leaving group, such as chloro.

Compounds of formula (3a) can be prepared by reacting a compound of formula (2):

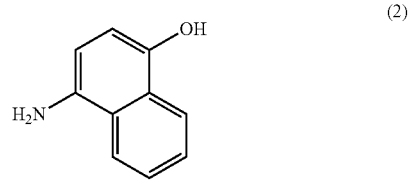 [SMILES: Nc1ccc(O)c2ccccc12]
(2)

with a compound of formula (D):

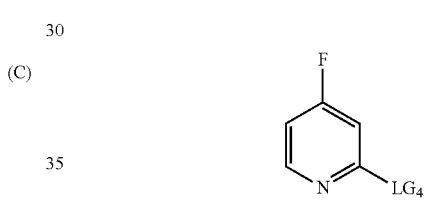
(D)

wherein LG$_4$ represents a leaving group, for example a halogen atom, such as chlorine, as per the compound of formula (3), under appropriate reaction conditions, for example in the presence of a strong base such as potassium tert-butoxide and N-methylpyrrolidone (1-methylpyrrolidin-2-one).

The compound of formula (1) can also be prepared by the process represented in Scheme 2:

Scheme 2

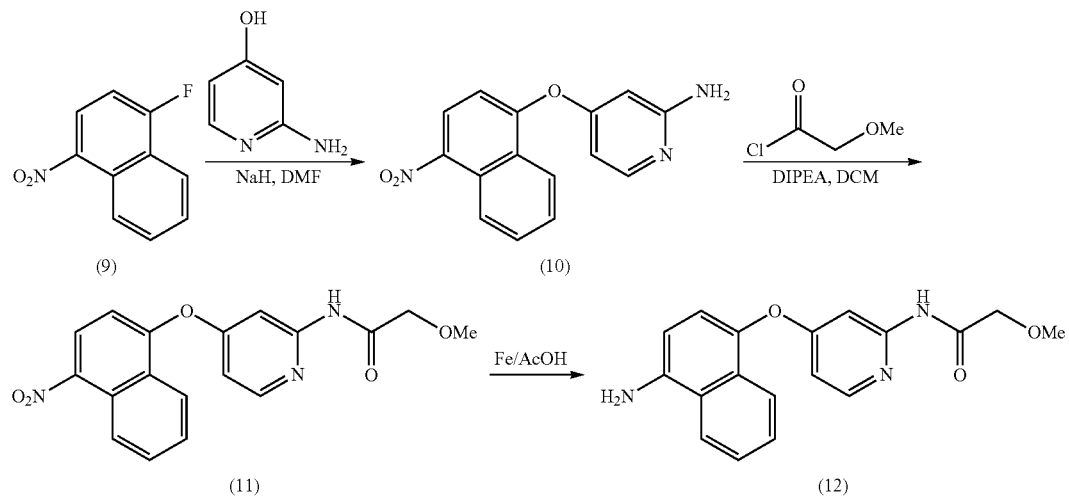

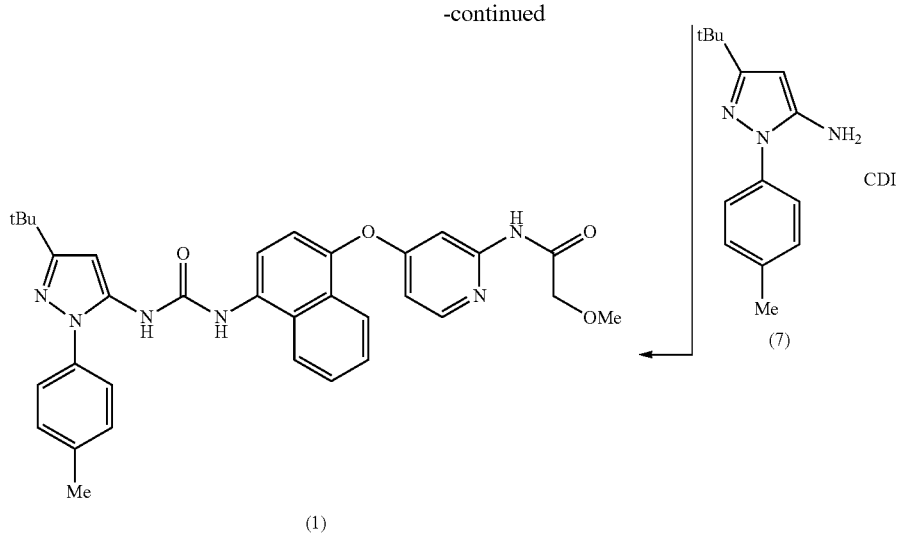

Thus the compound of formula (1) can be prepared by reacting a compound of formula (7):

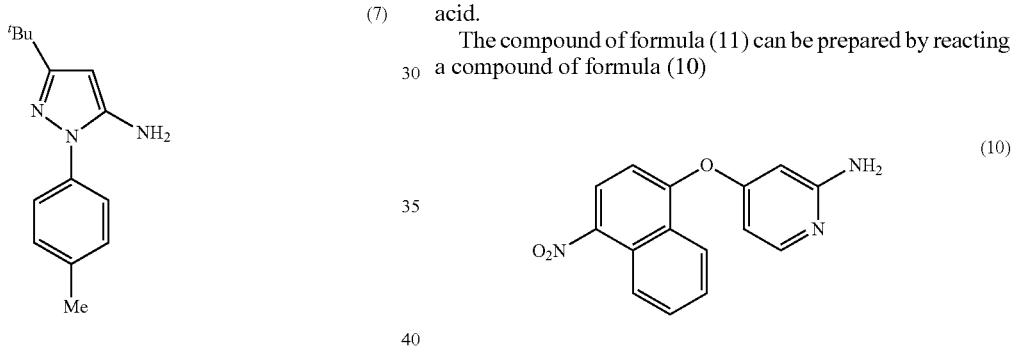

with a compound of formula (12):

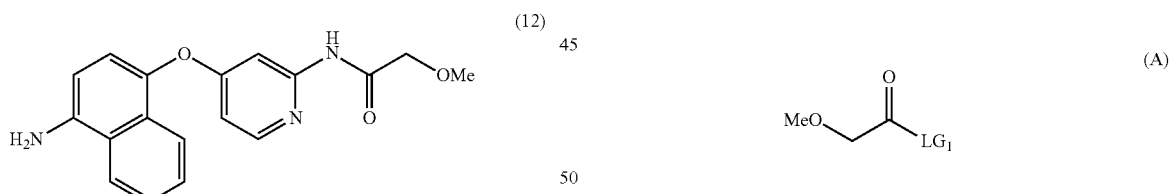

for example in the presence of a suitable coupling agent, such as 1,1-carbonyl-diimidazole.

The compound of formula (12) can be prepared by the reduction of a compound of formula (11):

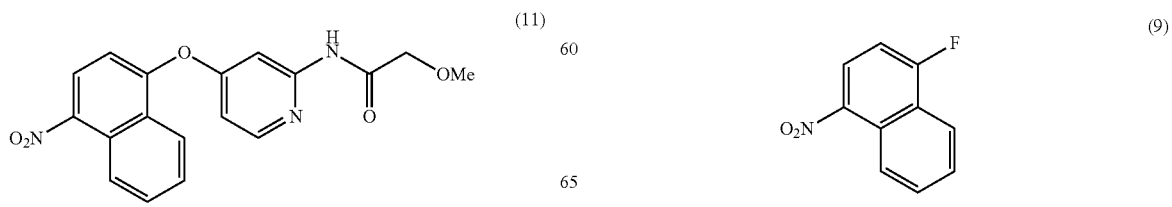

The reduction may be performed under hydrogenation conditions over a suitable catalyst such as palladium on carbon, or alternatively may be performed chemically using an appropriate reducing agent, such as iron powder in acetic acid.

The compound of formula (11) can be prepared by reacting a compound of formula (10)

with a compound of formula (A):

wherein $LG_1$ is represents a leaving group, as defined above.

The reaction may be performed in a suitable solvent, for example dichloromethane in the presence of a suitable non-nucleophilic base such as N,N-diisopropylethylamine.

The compounds of formula (10) can be prepared by reacting a compound of formula (9):

with a compound of formula (E):

wherein the group NR$^1$R$^2$ is an amine or a suitably protected derivative thereof, for example in the presence of a base such as sodium hydride and suitable solvent such as DMF. Where NR$^1$R$^2$ is not —NH$_2$, it will be appreciated that a suitable deprotection step must be included to provide the compound of formula (10).

Compounds of formulae (2), (7), (9), (A), (B), (C), (D) and (E) are either commercially available, or are known, or are novel and can be readily prepared by conventional methods. See for example Regan, J. et al.; *J. Med. Chem.*, 2003, 46, 4676-4686, WO00/043384, WO2007/087448 and WO2007/089512.

Protective groups may be required to protect chemically sensitive groups during one or more of the reactions described above, to ensure that the process can be carried out and/or is efficient. Thus if desired or necessary, intermediate compounds may be protected by the use of conventional protective groups. Protective groups and the means for their removal are described in "Protective Groups in Organic Synthesis", by Theodora W. Greene and Peter G. M. Wuts, published by John Wiley & Sons Inc; 4$^{th}$ Rev Ed., 2006, ISBN-10: 0471697540.

Novel intermediates as described herein form an aspect of the invention.

The compound of formula (1) is a p38 MAP kinase inhibitor and in one aspect the compound is useful in treatment of diseases, for example COPD and/or asthma.

Surprisingly, the compound seems to have a long duration of action and/or persistence of action in comparison to other known p38 MAP kinase inhibitors such as BIRB796.

In one embodiment the compound of formula (1) is a p38 MAPK alpha and/or gamma sub-type inhibitor.

Persistence of action as used herein is related to the dissociation rate or dissociation constant of the compound from the target (such as a receptor). A low dissociation rate may lead to persistence.

A low dissociation rate in combination with a high association rate tends to provide potent therapeutic entities.

The compound of formula (1) may be potent in vivo.

Typically, the prior art compounds developed to date have been intended for oral administration. This strategy involves optimizing compounds which achieve their duration of action by an appropriate pharmacokinetic profile. This ensures that there is a sufficient drug concentration established and maintained after and between doses to provide clinical benefit. The inevitable consequence of this approach is that all body tissues, especially liver and gut, are likely to be exposed to therapeutically active concentrations of the drug, whether or not they are adversely affected by the disease being treated.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by (i) ensuring that the drug has a sustained duration of action and is retained in the relevant organ to minimize the risks of systemic toxicity or (ii) producing a formulation which generates a "reservoir" of the active drug which is available to sustain the drug's desired effects. Approach (i) is exemplified by the anticholinergic drug tiotropium (Spiriva), which is administered topically to the lung as a treatment for COPD, and which has an exceptionally high affinity for its target receptor resulting in a very slow off rate and a consequent sustained duration of action.

In one aspect of the disclosure the compound of formula (1) is particularly suitable for topical delivery, such as topical delivery to the lungs, in particular for the treatment of respiratory disease, for example chronic respiratory disease such as COPD and/or asthma.

In one embodiment the compound of formula (1) is suitable for sensitizing patients to treatment with a corticosteroid who have become refractory to such treatment regimens.

The compound of formula (1) may also be useful for the treatment of rheumatoid arthritis.

The compound of formula (1) may have antiviral properties, for example the ability to prevent infection of cells (such as respiratory epithelial cells) with a picornavirus, in particular a rhinovirus, influenza or respiratory synctial virus.

Thus the compound is thought to be an antiviral agent, in particular suitable for the prevention, treatment or amelioration of picornavirus infections, such as rhinovirus infection, influenza or respiratory syncitial virus.

In one embodiment the compound of formula (1) is able to reduce inflammation induced by viral infection, such as rhinovirus infection and in particular viral infections that result in the release of cytokines such as IL-8, especially in vivo. This activity may, for example be tested in vitro employing a rhinovirus induced IL-8 assay as described in the Examples herein.

In one embodiment the compound of formula (1) is able to reduce ICAM1 expression induced by rhinovirus, especially in vivo. ICAM1 is the receptor mechanism used by so-called major groove rhinovirus serotypes to infect cells. This activity may be measured, for example by a method described in the Examples herein.

It is expected that the above properties render the compound of formula (1) particularly suitable for use in the treatment and/or prophylaxis of exacerbations, in particular viral exacerbations, in patients with one or more the following chronic conditions such as congestive heart failure, COPD, asthma, diabetes, cancer and/or in immunosuppressed patients, for example post-organ transplant.

In particular, the compound of formula (1) may be useful in the treatment of one or more respiratory disorders including COPD (including chronic bronchitis and emphysema), asthma, pediatric asthma, cystic fibrosis, sarcoidosis, idiopathic pulmonary fibrosis, allergic rhinitis, rhinitis, sinusitis, especially asthma, and COPD (including chronic bronchitis and emphysema).

The compound of formula (1) may also be useful in the treatment of one or more conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

It is also expected that the compound of formula (1) may be useful in the treatment of certain other conditions including rheumatoid arthritis, pancreatitis cachexia, inhibition of the growth and metastasis of tumours including non-small cell lung carcinoma, breast carcinoma, gastric carcinoma, colorectal carcinomas and malignant melanoma.

The compound of formula (1) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (1) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoro methane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 microns. The formulation will typically contain a topically acceptable diluent such as lactose, usually of large particle size e.g. an MMAD of 100 μm or more. Examples of dry powder delivery systems include SPINHALER, DISKHALER, TURBOHALER, DISKUS and CLICKHALER.

The compound of formula (1) has therapeutic activity. In a further aspect, the present invention provides a compound of the disclosure for use as a medicament. Thus, in a further aspect, the present invention provides a compound as described herein for use in the treatment of one or more of the above mentioned conditions.

In a further aspect, the present invention provides use of a compound as described herein for the manufacture of a medicament for the treatment of one or more of the above mentioned conditions.

In a further aspect, the present invention provides a method of treatment of one or more of the above mentioned conditions which comprises administering to a subject an effective amount of a compound of the disclosure or a pharmaceutical composition comprising the compound.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline). Other suitable actives include anticholinergics, such as tiotropium and anti-viral agents such as, but not limited to, zanamivir or oseltamivir, for example as the phosphate. Other anti-viral agents include peramivir and laninamivir.

The data generated below in relation to the antiviral properties of the compound of formula (1) leads the inventors to believe that other antiviral therapies would be useful in the treatment or prevention of exacerbations of patients with respiratory disease such as COPD and/or asthma and/or one or more of the indications listed above. Thus in one aspect there is provided the use of an anti-viral therapy, such as, but not limited to, zanamavir or oseltamivir (for example oseltamivir phosphate), in the treatment or prevention of respiratory viral infections in patients with chronic conditions such as congestive heart failure, diabetes, cancer, or in immunosuppressed patients, for example post-organ transplant.

ABBREVIATIONS

AcOH glacial acetic acid
Aq aqueous
Ac acetyl
ATP adenosine-5'-triphosphate
BALF bronchoalveolae lavage fluid
Br broad
BSA bovine serum albumin
CatCart® catalytic cartridge
CDI 1,1-carbonyl-diimidazole
COPD chronic obstructive pulmonary disease
D doublet
$Pd_2(dba)_3$ Tris(dibenzylideneacetone)dipalladium
DCM dichloromethane
DIAD diisopropylazadicarboxylate
DIBAL-H diisobutylaluminum hydride
DMAP N,N-dimethylpyridin-4-amine
DIPEA N,N-diisopropylethylamine
DMF N,N-dimethylformamide
DMSO dimethyl sulfoxide
ELISA enzyme immunosorbent assay
EtOAc ethyl acetate
FCS foetal calf serum
FRET fluorescence resonance energy transfer
HEPES 2-(4-(2-hydroxyethyl)piperazin-1-yl)ethanesulfonic acid
Hr hour(s)
HRP horseradish peroxidase
HRV human rhinovirus
ICAM1 intercellular adhesion molecule 1
IgG immunoglobin G
IL-8 interleukin 8
JNK c-Jun N-terminal kinase
LPS lipopolysaccharide
MAPK mitogen protein activated protein kinase
MAPKAP-K2 mitogen-activated protein kinase-activated protein kinase 2
MeOH methanol
Min minute(s)
MTT 3-(4,5-Dimethylthiazol-2-yl)-2,5-diphenyltetrazolium bromide
NMP N-methylpyrrolidone (1-methylpyrrolidin-2-one)
NSE no significant effect
OD optical density
PBMC peripheral blood mononuclear cell
PBS phosphate buffered saline
PMA phorbol myristate acetate
$PPh_3$ triphenylphosphine
RSV respiratory syncitial virus
RT room temperature
RP HPLC reverse phase high performance liquid chromatography
S singlet
SCX solid supported cation exchange
SDS sodium dodecyl sulfate
$SiO_2$ silica gel
T triplet
$TCID_{50}$ 50% tissue culture infection dose
TFA trifluoroacetic acid
THF tetrahydrofuran
TMB 3,3",5,5"-tetramethylbenzidine
TNFα tumor necrosis factor alpha
XantPhos 4,5-bis(diphenylphosphino)-9,9-dimethylxanthene General Procedures All starting materials and solvents were either obtained from commercial sources or prepared according to the literature citation. Hydrogenations were preformed on a Thales H-cube flow reactor under the conditions stated. Organic solutions were routinely dried over magnesium sulfate. SCX was purchased with Supelco and treated with 1M aqueous HCl prior to use. The reaction mixture to be purified was first diluted with MeOH and made acidic with a few drops of AcOH. This solution was loaded directly onto the SCX and washed with MeOH. The desired material was then eluted by washing with 1% $NH_3$ in MeOH. Column chromatography was performed on Silicycle pre-packed silica (230-400 mesh, 40-63 μM) cartridges using the amount indicated.

Preparative Reverse Phase High Performance Liquid Chromatography:

Agilent Scalar column C18, 5 μm (21.2×50 mm), flow rate 28 mL/min eluting with a $H_2O$-MeCN gradient containing 0.1% v/v formic acid over 10 mins using UV detection at 215 and 254 nm. Gradient information: 0.0-0.5 min: 95% $H_2O$-5% MeCN; 0.5-7.0 min; Ramped from 95% $H_2O$-5% MeCN to 5% $H_2O$-95% MeCN; 7.0-7.9 min: Held at 5% $H_2O$-95% MeCN; 7.9-8.0 min: Returned to 95% $H_2O$-5% MeCN; 8.0-10.0 min: Held at 95% $H_2O$-5% MeCN.

Analytical Methods

Reverse Phase High Performance Liquid Chromatography:

Agilent Scalar column C18, 5 μm (4.6×50 mm) or Waters XBridge C18, 5 μm (4.6×50 mm) flow rate 2.5 mL/min eluting with a $H_2O$-MeCN gradient containing 0.1% v/v formic acid over 7 min employing UV detection at 215 and 254 nm. Gradient information: 0.0-0.1 min: 95% $H_2O$-5% MeCN; 0.1-5.0 min; Ramped from 95% $H_2O$-5% MeCN to 5% $H_2O$-95% MeCN; 5.0-5.5 min: Held at 5% $H_2O$-95% MeCN; 5.5-5.6 min: Held at 5% $H_2O$-95% MeCN, flow rate increased to 3.5 ml/min; 5.6-6.6 min: Held at 5% $H_2O$-95% MeCN, flow rate 3.5 ml/min; 6.6-6.75 min: Returned to 95% $H_2O$-5% MeCN, flow rate 3.5 ml/min; 6.75-6.9 min: Held at 95% $H_2O$-5% MeCN, flow rate 3.5 ml/min; 6.9-7.0 min: Held at 95% $H_2O$-5% MeCN, flow rate reduced to 2.5 ml/min.

$^1$H NMR Spectroscopy:

Bruker Avance III 400 MHz using residual undeuterated solvent as reference

Experimental Procedures for Scheme 1

4-(2-Chloropyridin-4-yloxy)naphthalen-1-amine (3)

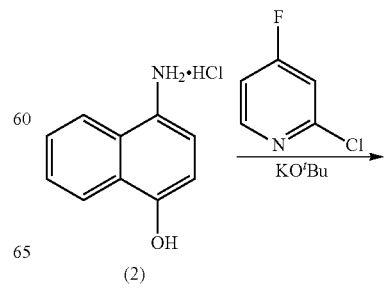

(2)

17
-continued

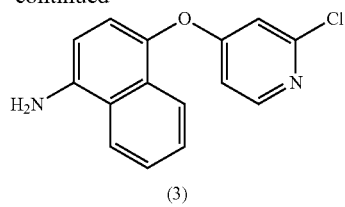

(3)

To a stirred solution of 2-chloro-4-fluoropyridine (1.261 g, 9.58 mmol) and 4-amino-1-naphthol hydrochloride (2) (750 mg, 3.83 mmol) in NMP (40 mL), at −20° C., was added potassium tert-butoxide (1.290 g, 11.50 mmol). The reaction mixture was allowed to warm to RT. After 2.5 hr, the reaction mixture was diluted with water (100 mL) and extracted with EtOAc (100 mL then 2×80 mL). The combined organic extracts were washed with brine (150 mL), dried and evaporated in vacuo. The crude product was subjected to SCX capture and release eluting with 1% NH$_3$ in MeOH solution and the solvent was removed in vacuo to give 4-(2-chloropyridin-4-yloxy)naphthalen-1-amine (3) (1.019 g, 92%) as a brown solid: m/z 271 (M+H)$^+$ (ES$^+$).

4-(2-Chloropyridin-4-yloxy)naphthalen-1-N,N-di-tert-butylcarbamate (4)

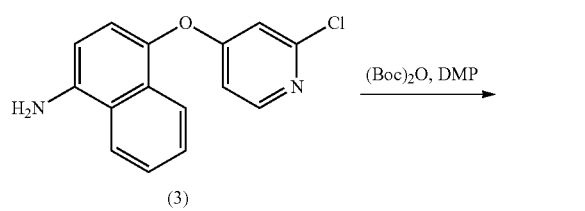

To a stirred solution of 4-(2-chloropyridin-4-yloxy)naphthalen-1-amine (3) (1.019 g, 3.76 mmol) in THF (30 mL) at 0° C. was added DMAP (0.034 g, 0.282 mmol) and then di-tert-butyl dicarbonate (0.904 g, 4.14 mmol). The reaction mixture was stirred at 0° C. for 30 min, and then allowed to warm to RT. After 1.5 hr, the reaction mixture was cooled to 0° C., and further di-tert-butyl dicarbonate (0.904 g, 4.14 mmol) was added. The resulting mixture was stirred at 0° C. for 15 min and then at RT. After 16 hr the reaction mixture was diluted with water (40 mL) and extracted with EtOAc (2×40 mL). The combined organic extracts were washed with brine (75 mL), dried and evaporated in vacuo. The crude material was purified by flash column chromatography (SiO$_2$; 80 g) eluting with 0 to 40% EtOAc in iso-hexane to give 4-(2-chloropyridin-4-yloxy)naphthalen-1-N,N-di-tert-butylcarbamate (4) (0.892 g, 48%) as a purple solid: m/z 471 (M+H)$^+$ (ES$^+$).

18
tert-Butyl 4-(4-(N,N-di-tert-butylcarbamyl)naphthalen-1-yloxy)pyridin-2-ylcarbamate (5)

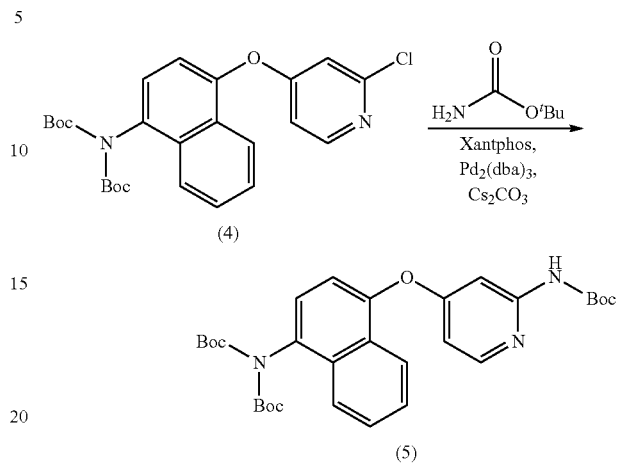

A mixture of 4-(2-chloropyridin-4-yloxy)naphthalen-1-N,N-di-tert-butylcarbamate (4) (0.892 g, 1.894 mmol), tert-butyl carbamate (0.666 g, 5.68 mmol), caesium carbonate (0.926 g, 2.84 mmol), Pd$_2$(dba)$_3$ (0.043 g, 0.047 mmol) and XantPhos (0.055 g, 0.095 mmol) was suspended in THF (10 mL). The reaction mixture was purged thoroughly with nitrogen, and then heated at reflux. After 15 hr the mixture was cooled to RT, diluted with water (35 mL) and extracted with EtOAc (35 mL, 25 mL). The combined organic extracts were washed with brine (50 mL), dried and evaporated in vacuo. The crude material was purified by flash column chromatography (SiO$_2$; 80 g) eluting with 0 to 30% EtOAc in iso-hexane to give tert-butyl 4-(4-(N,N-di-tert-butylcarbamyl)naphthalen-1-yloxy)pyridin-2-ylcarbamate (5) (289 mg, 28%) as a white solid: m/z 552 (M+H)$^+$ (ES$^+$).

4-(4-Aminonaphthalen-1-yloxy)pyridin-2-amine (6)

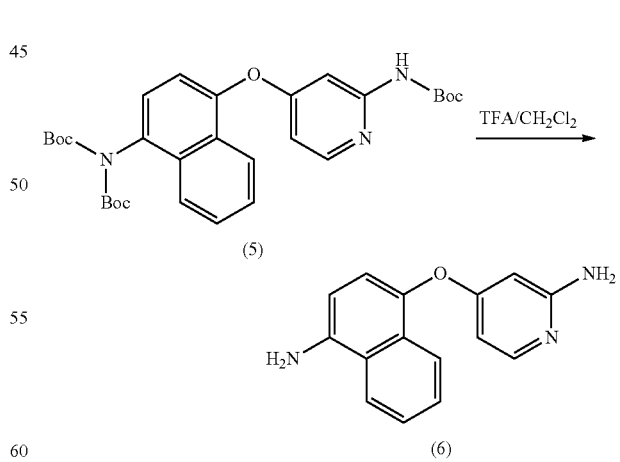

To a stirred solution of tert-butyl 4-(4-(N,N-di-tert-butylcarbamyl)naphthalen-1-yloxy)pyridin-2-ylcarbamate (5) (289 mg, 0.524 mmol) in DCM (8 mL), at 0° C., was added TFA (4 mL). The resulting mixture was stirred while slowly warming to RT. After 5 hr, the volatiles were removed in vacuo and the residue was taken up in MeOH (5 mL) and subjected to SCX capture and release eluting with 1% NH₃ in MeOH solution. The solvent was removed in vacuo to afford 4-(4-aminonaphthalen-1-yloxy)pyridin-2-amine (6) (116 mg, 85%) as a brown-orange oil: m/z 252 (M+H)⁺ (ES⁺).

1-(4-(2-aminopyridin-4-yloxy)naphthalen-1-yl)-3-(3-tert-butyl-1-p-tolyl-1H-pyrazol-5-yl)urea (8)

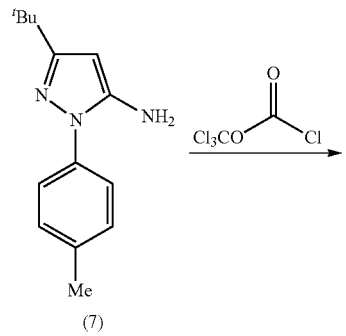

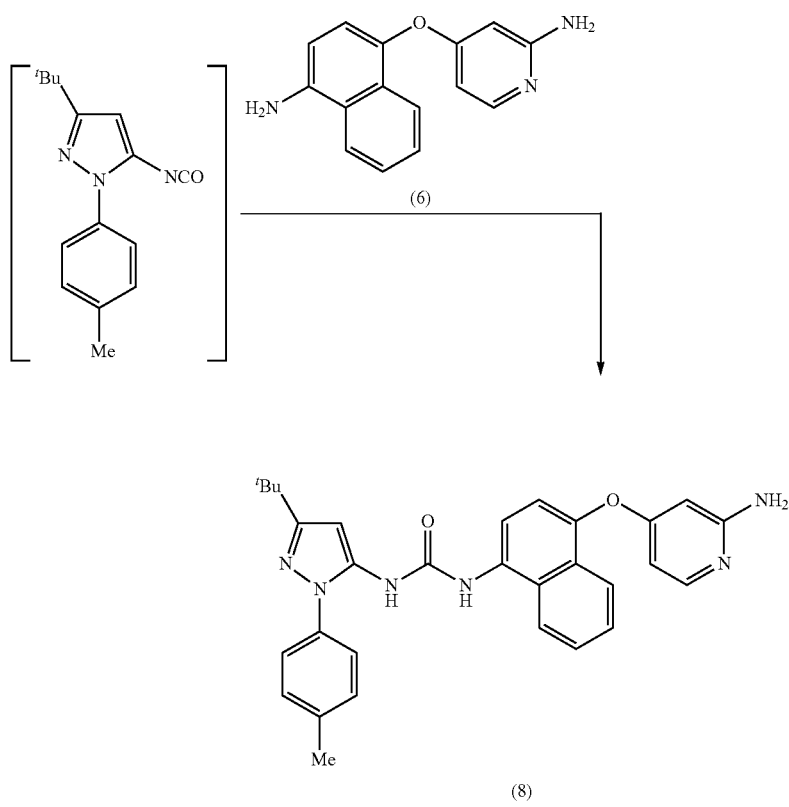

To a stirred solution of 4-(4-aminonaphthalen-1-yloxy)pyridin-2-amine (6) (116 mg, 0.462 mmol) and DIPEA (241 μl, 1.385 mmol) in THF (3 mL), at 0° C., was added an aliquot of the isocyanate solution prepared above (2 mL, 0.300 mmol). The resulting mixture was stirred while slowly warming to RT. Additional aliquots of the isocyanate solution in THF were added to the reaction mixture after 1.5 hr, (1 mL, 0.150 mmol) and after a further 3.5 hr (0.5 mL, 0.075 mmol). After A saturated solution of NaHCO₃ (14 mL) was added to a solution of 5-aminopyrazole (7) (0.206 g, 0.900 mmol) in DCM (20 mL). The mixture was stirred vigorously, cooled to 0° C. and trichlbromethylchloroformate (0.326 mL, 2.70 mmol) was added in one portion. The reaction mixture was stirred vigorously at 0° C. for a further 80 min. The layers were separated and the organic layer was dried, evaporated in vacuo and the resulting orange oil was dried further for 30 min under high vacuum. The isolated isocyanate was then taken up into THF (6 mL) and kept under nitrogen at 0° C.

20 hr water (30 mL) was added and the mixture was extracted with EtOAc (2×30 mL). The combined organic extracts were washed with brine (50 mL), dried and evaporated in vacuo. The crude material was purified by flash column chromatography (SiO₂; 12 g) eluting with 25 to 100% [5% MeOH in EtOAc] in iso-hexane to furnish 1-(4-(2-aminopyridin-4-yloxy)naphthalen-1-yl)-3-(3-tert-butyl-1-p-tolyl-1H-pyrazol-5-yl)urea (8) (127 mg, 49%) as a brown oil: m/z 507 (M+H)⁺ (ES⁺).

N-(4-(4-(3-(3-tert-Butyl-1-p-tolyl-1H-pyrazol-5-yl)ureido)naphthalen-1-yloxy)pyridin-2-yl)-2-methoxy-acetamide (1)

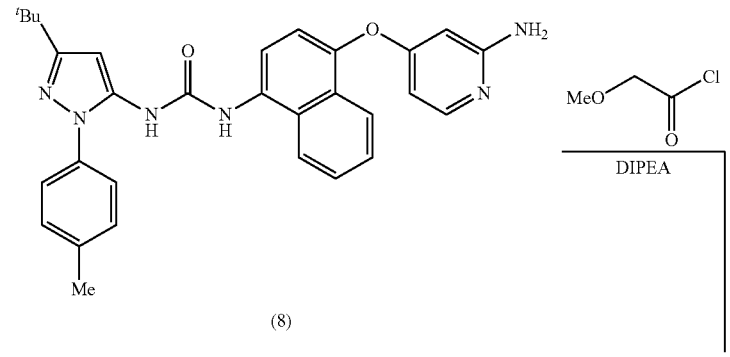

(8)

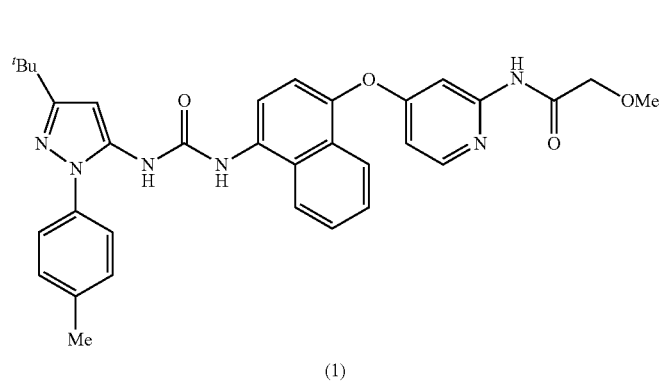

(1)

Methoxyacetyl chloride (64.2 μl, 0.703 mmol) was added slowly to a mixture of 1-(4-(2-aminopyridin-4-yloxy)naphthalen-1-yl)-3-(3-tert-butyl-1-p-tolyl-1H-pyrazol-5-yl)urea (8) (89 mg, 0.176 mmol) and DIPEA (153 μl, 0.878 mmol) in THF (5 mL). The reaction mixture was stirred at 0° C. for a further 20 min and then warmed to RT. After 2.5 hr, the reaction was quenched by the addition of a solution of 1% $NH_3$ in MeOH (3 mL), and the resulting mixture stirred for a further 45 min. The volatiles were removed in vacuo and the residue was dissolved in a mixture of MeOH (5 mL) and AcOH (2 mL) and subjected to SCX capture and release eluting with 1% $NH_3$ in MeOH solution. The crude material was purified by flash column chromatography ($SiO_2$; 12 g) eluting with 0 to 60% [5% MeOH in EtOAc] in iso-hexane to give N-(4-(4-(3-(3-tert-butyl-1-p-tolyl-1H-pyrazol-5-yl)ureido)naphthalen-1-yloxy)pyridin-2-yl)-2-methoxyacetamide (1) (62 mg, 61%) as a white solid: m/z 579 (M+H)$^+$ (ES$^+$). $^1$H NMR (400 MHz, DMSO-$d_6$) δ: 1.29 (9H, s), 2.40 (3H, s), 3.31 (3H, s), 3.99 (2H, s), 6.41 (1H, s), 6.70 (1H, dd), 7.32-7.40 (3H, m), 7.44-7.48 (2H, m), 7.55-7.61 (1H, m), 7.63-7.67 (2H, m), 7.84 (1H, dd), 7.97 (1H, d), 8.09 (1H, d), 8.19 (1H, d), 8.79 (1H, s), 9.13 (1H, s), 10.02 (1H, s).

Experimental Procedures for Scheme 2

4-(4-Nitronaphthalen-1-yloxy)pyridin-2-amine (10)

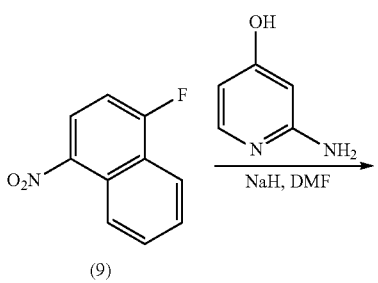

(9)

-continued

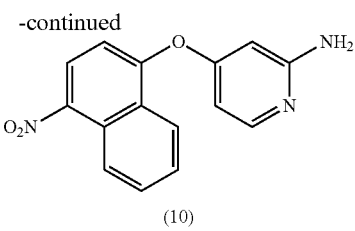

(10)

To a stirred solution of 2-aminopyridine-4-ol (23.0 g, 209 mmol) in DMF (200 mL) at 0° C., under nitrogen was added NaH (60% dispersion in mineral oil, 9.21 g, 230 mmol) in portions over 30 mins. The mixture was warmed to RT and after 1 hr cooled to 0° C. and a solution of 1-fluoro-4-nitronaphthylene (9) (40.0 g, 209 mmol) in DMF (100 mL) was added. The reaction mixture was allowed to warm to RT and after 1.5 hr it was diluted with water (1 L) and extracted with EtOAc (3×500 mL). The organic extracts were combined and washed with water (3×700 mL) and brine (500 mL). A yellow precipitate separated which was collected by filtration and washed with water (500 mL) and dried in vacuo overnight. The organic layer was dried (MgSO$_4$), filtered and evaporated in vacuo. The residue was triturated with a mixture of acetonitrile (20 mL) and ether (200 mL) to give a red solid which was washed with isohexane (200 mL). The supernatant liquor from the trituration was evaporated in vacuo and the residue was purified by flash column chromatography (SiO$_2$, 120 g, 30-100% EtOAc in isohexane, gradient elution). This product was combined with the two solids isolated previously, taken up into MeOH (500 mL) and evaporated in vacuo to afford 4-(4-nitronaphthalen-1-yloxy)pyridin-2-amine (10) (40.1 g, 65%) as a yellow solid: m/z 282 (M+H)$^+$ (ES$^+$).

2-Methoxy-N-(4-(4-nitronaphthalen-1-yloxy)pyridin-2-yl)acetamide (11)

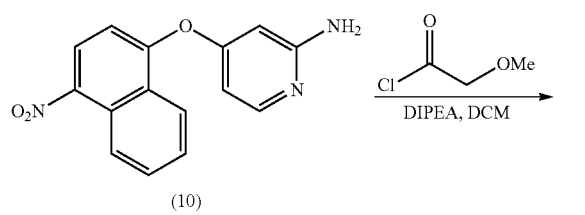

To a stirred solution of 4-(4-nitronaphthalen-1-yloxy)pyridin-2-amine (10) (40.0 g, 135 mmol) and DIPEA (48.1 mL, 270 mmol) in DCM (600 mL) at 0° C., under nitrogen, was added dropwise methoxyacetyl chloride (18.53 ml, 203 mmol). The mixture was warmed to RT and after 1 hr a solution of ammonia (100 mL, 7 M in MeOH) was added and stirring continued for 30 min, during which time a precipitate formed. The mixture was evaporated in vacuo and water (1 L) was added to the residue to provide a red suspension. Glacial acetic acid was added dropwise until a yellow colour persisted (~5 mL). The solid was collected by filtration and washed with water (300 mL) to afford 2-methoxy-N-(4-(4-nitronaphthalen-1-yloxy)pyridin-2-yl)acetamide (11) (44.1 g, 90%) as a yellow solid: m/z 354 (M+H)$^+$ (ES$^+$).

N-(4-(4-Aminonaphthalen-1-yloxy)pyridin-2-yl)-2-methoxyacetamide (12)

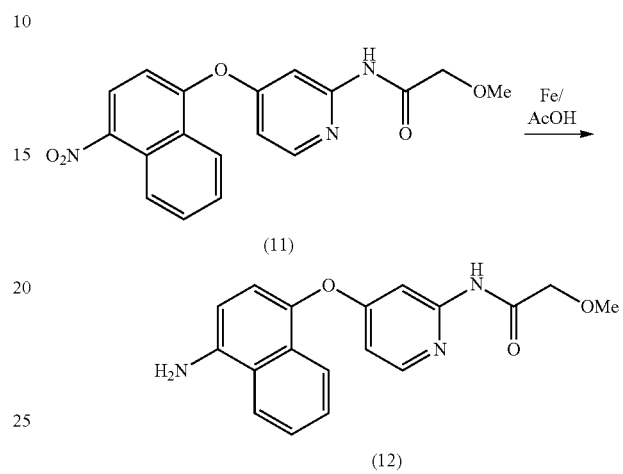

A stirred suspension of 2-methoxy-N-(4-(4-nitronaphthalen-1-yloxy)pyridin-2-yl)acetamide (11) (44.0 g, 125 mmol) and iron powder (41.7 g, 747 mmol) in acetic acid (300 mL) was heated at 45° C. After 3 hr the mixture was cooled to RT and poured slowly and cautiously onto solid Na$_2$CO$_3$ (200 g). The mixture effervesced vigorously. The mixture was partitioned between water (500 mL) and EtOAc (500 mL). The aqueous layer was basified with solid Na$_2$CO$_3$ to pH 11 and filtered through a pad of celite. The aqueous layer and celite pad were extracted with EtOAc (3×500 mL) and the combined extracts were washed with saturated aqueous NaHCO$_3$ solution (500 mL), dried (MgSO$_4$) and evaporated in vacuo to afford N-(4-(4-aminonaphthalen-1-yloxy)pyridin-2-yl)-2-methoxyacetamide (12) (35.0 g, 78%) as a purple foam: m/z 324 (M+H)$^+$ (ES$^+$).

N-(4-(4-(3-(3-tert-Butyl-1-p-tolyl-1H-pyrazol-5-yl)ureido)naphthalen-1-yloxy)pyridin-2-yl)-2-methoxyacetamide (1)

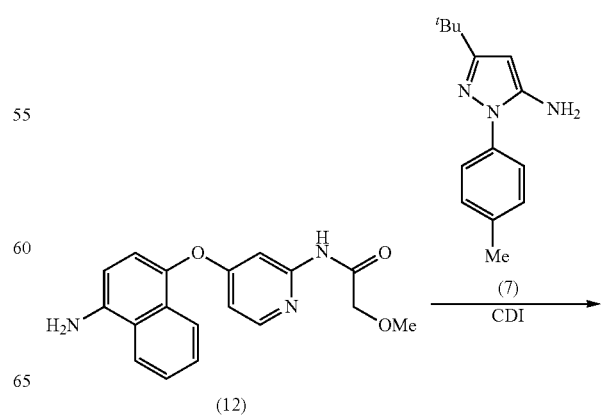

-continued

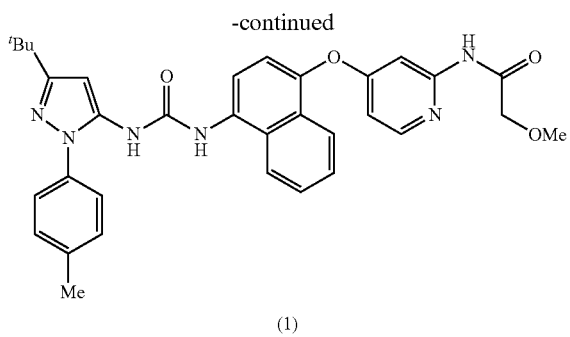

(1)

To a stirred suspension of CDI (28.8 g, 178 mmol) in DCM (250 mL) at RT, under nitrogen, was added 3-tert-butyl-1-p-tolyl-1H-pyrazol-5-amine (7) (40.7 g, 178 mmol) portionwise over 1 hr. After 1 hr the resulting dark red solution was added dropwise, over 1 hr, to a stirred solution of N-(4-(4-aminonaphthalen-1-yloxy)pyridin-2-yl)-2-methoxyacetamide (12) (35.5 g, 99 mmol) in DCM (1 L). After 1 hr MeOH (100 mL) was added and the mixture was kept at RT for 16 hr. The reaction mixture was evaporated in vacuo and the residue was taken up into DCM (500 mL) and was washed with water and saturated aqueous $NaHCO_3$ solution (500 mL). The organic layer was dried ($MgSO_4$), evaporated in vacuo and the residue purified by flash column chromatography ($SiO_2$, 800 g, 2% MeOH in DCM, isocratic elution). This product was recrystallized from ethyl acetate/heptane (800 mL of a 5:3 v/v mixture) to afford N-(4-(4-(3-(3-tert-butyl-1-p-tolyl-1H-pyrazol-5-yl)ureido)naphthalen-1-yloxy)pyridin-2-yl)-2-methoxyacetamide (1) (25.5 g, 45%) as a white powder. Found: C, 68.41; H, 5.93; N, 14.36; $C_{33}H_{34}N_6O_4$ requires: C, 68.49; H, 5.92; N, 14.52%.

Biological Testing

Summaries of the properties of the compound of formula (1) established using in vitro assays are presented below. The compound of formula (1) showed substantial differences in its profiles to BIRB796. Although both compounds were potent and effective inhibitors of LPS-induced TNFα release in THP-1 cells and differentiated U937 cells (Table 1), BIRB796 showed no significant effect (NSE) in the six other systems we investigated, namely: LPS-induced IL-8 release in differentiated U937 cells (BIRB796 31% of maximum inhibition; the compound of formula (1) $IC_{50}$: 7.9 nM); LPS-induced IL-8 release from sputum macrophages (Table 2); poly I:C induced ICAM1 expression in human bronchial epithelial cell line, BEAS2B cells (BIRB796 no effect at 10 ug/ml; the compound of formula (1) $IC_{50}$: 1.7 nM), rhinovirus-induced ICAM1 expression in BEAS2B cells (Table 2); rhinovirus-induced IL-8 release in BEAS2B cells (Table 2) and rhinovirus replication in MRC5 cells. In marked contrast, the compound of formula (1) demonstrated activity in all six systems and showed levels of potency which were equivalent to or exceeded those in demonstrated in LPS-induced TNFα release in U937 cells.

TABLE 1

Comparative p38 MAP kinase activity and LPS induced TNF-α activity of macrophages for BIRB796 and Compound (1)

| Test Compound | $IC_{50}$ Values (nM) | | | |
| --- | --- | --- | --- | --- |
| | p38 MAPK Enzymes | | LPS-induced TNFα release | |
| | α subtype | γ subtype | d-U937 cells[a] | THP1 cells |
| BIRB796 | 12 (n = 6) | 296 (n = 5) | 20 (n = 2) | 12 (n = 3) |
| (1) | 12 (n = 2) | 344 (n = 2) | 2.1 (n = 3) | 13 (n = 3) |

[a]d-U937 cells = Differentiated U937 cells

TABLE 2

Comparative Anti-Inflammatory Activity of BIRB796 and Compound (1)

| Test Compound | $IC_{50}$ Values (nM) | | |
| --- | --- | --- | --- |
| | Sputum macrophages LPS-induced IL-8 release | BEAS2B cells | |
| | | Rhinovirus-induced ICAM expression | Rhinovirus-induced IL-8 release |
| BIRB796 | NSE @ 19 μM (n = 2) | NSE @ 1.9 μM (n = 2) | NSE @ 1.9 μM (n = 2) |
| (1) | 5 (n = 1) | 0.37 (n = 4) | 0.065 (n = 4) |

The potential of these two compounds to inhibit rhinovirus replication in human fetal lung fibroblast, MRC5 cells has been investigated further. It was established that BIRB796 was without effect on viral replication over a concentration range up to 1.9 μM. However, we investigated the concentration effect curves of the compound of formula (1) and found that a concentration of 5.2 nM decreased the viral titre by 1 log order.

A description of these assays is as follows:

Enzyme Inhibition Assay

The enzyme inhibitory activity of compound was determined by FRET using synthetic peptides labelled with both donor and acceptor fluorophores (Z-LYTE, Invitrogen Ltd., Paisley, UK). Recombinant, phosphorylated p38 MAPK γ (MAPK12:Millipore) was diluted in HEPES buffer, mixed with compound at desired final concentrations and incubated for two hours at room temperature. The FRET peptide (2 μM) and ATP (100 μM) were next added to the enzyme/compound mixture and incubated for 1 hr. Development reagent (protease) was added for 1 hr prior to detection in a fluorescence microplate reader (Varioskan® Flash, ThermoFisher Scientific). The site-specific protease cleaves only non-phosphorylated peptide and eliminates the FRET signal. Phosphorylation levels of each reaction were calculated using the ratio of coumarin emission (donor) over fluorescein emission (acceptor) with high ratios indicating high phosphorylation and low ratios, low phosphorylation levels. The percentage inhibition of each reaction was calculated relative to non-inhibited control, and the 50% inhibitory concentration ($IC_{50}$ value) then calculated from the concentration-response curve.

For p38 MAPK alpha (MAPK14: Invitrogen), enzyme activity was evaluated indirectly by determining activation/phosphorylation of the down-stream molecule, MAPKAP-K2. The p38 MAPKαprotein was mixed with the test compound for 2 hr at RT. The p38α inactive target MAPKAP-K2 (Invitrogen) and FRET peptide (2 μM), which is a phosphorylation target for MAPKAP-K2, and ATP (10 μM) were then added to the enzymes/compound mixture and incubated for one hour. Development reagent was then added and the mixture incubated for one hour before detection by fluorescence completed the assay protocol.

LPS-Induced TNF α Release in U937 Cells and THP-1 Cells: Potency

U937 cells, human monocytic cell line, were differentiated to macrophage-type cells by incubation with phorbol myristate acetate (PMA; 100 ng/ml) for 48 to 72 hr. Where appropriate, cells were pre-incubated with final concentrations of compound for 2 hr. Cells were then stimulated with 0.1 μg/ml of LPS (from E. Coli: O111:B4, Sigma) for 4 hr, and the supernatant collected for determination of TNFα concentration by sandwich ELISA (Duo-set, R&D systems). The inhibition of TNFα production was calculated as a percentage of that achieved by 10 μg/ml of BIRB796 at each concentration of test compound by comparison with vehicle control. The relative 50% effective concentration (R-EC$_{50}$) was determined from the resultant concentration-response curve. THP-1, human monocytic cell line, was also used for this assay. THP-1 cells were stimulated with 3 µg/ml of LPS (from E. Coli: O111:B4, Sigma) for 4 hr, and the supernatant collected for determination of TNFα concentration.

The 50% inhibitory concentration (IC$_{50}$) was determined from the resultant concentration-response curve.

LPS-Induced IL-8 Release in U937 Cells: Potency

U937 cells, human monocytic cell line, were differentiated to macrophage-type cells by incubation with phorbol myristate acetate (PMA; 100 ng/ml) for 48 to 72 hours. Cells were pre-incubated with final concentrations of compound for 2 hrs. Cells were then stimulated with 0.1 µg/ml of LPS (from E. Coli: O111:B4, Sigma) for 4 hrs, and the supernatant collected for determination of the IL-8 concentration by sandwich ELISA (Duo-set, R&D systems). The inhibition of IL-8 production was calculated at each concentration of test compound by comparison with vehicle control. The 50% inhibitory concentration (IC$_{50}$) was determined from the resultant concentration-response curve.

Poly I:C-induced ICAM-1 induction in BEAS2B cells: potency

Poly I:C (1 ug/ml) (Invivogen Ltd., San Diego, Calif.) was transfected into BEAS2B cells (human bronchial epithelial cells, ATCC) with Oligofectamine (Invitrogen, Carlsbad, Calif.). Cells were pre-incubated with final concentrations of compound for 2 hrs. The level of ICAM1 expression on the cell surface was determined by cell-based ELISA. Briefly, at 18 hrs after poly I:C transfection, cells were fixed with 4% formaldehyde in PBS. After quenching endogenous peroxidase by adding 0.1% sodium azide and 1% hydrogen peroxide, cells were washed with wash-buffer (0.1% Tween in PBS: PBS-Tween). After blocking the wells with 5% milk in PBS-Tween for 1 hr, the cells were incubated with anti-human ICAM-1 antibody (Cell Signaling Technology, Danvers, Mass.) in 1% BSA PBS overnight at 4° C. Cells were washed with PBS-Tween and incubated with the secondary antibody (HRP-conjugated anti-rabbit IgG, Dako Ltd., Glostrup, Denmark). The ICAM-1 signal was detected by adding substrate and reading the absorbance at 450 nm with a reference wavelength of 655 nm using a spectrophotometer. The cells were then washed with PBS-Tween and total cell numbers in each well were determined by reading absorbance at 595 nm after Crystal Violet staining and elution by 1% SDS solution. The measured OD 450-655 readings were corrected for cell number by dividing with the OD595 reading in each well. The inhibition of ICAM-1 expression was calculated at each concentration of test compound by comparison with vehicle control. The 50% inhibitory concentration (IC$_{50}$) was determined from the resultant concentration-response curve.

Sputum Macrophage Assay

Sputum was induced by inhalation of a nebulised solution of 3% (w/v) hypertonic saline to healthy volunteers. Dithiothreitol (0.02% at final) was then added and mixed vigorously using a vortex mixer until the sputum became less viscous. The cell pellet produced by centrifugation (at 1500 rpm for 10 min) was resuspended in 10% FCS RPMI-1640, and sputum macrophages were separated by plate adhesion in high binding plate (CellBIND®, Corning Limited. UK) for 2 hr. The adhered cells were washed with RPMI-1640, and stimulated with LPS (1 ug/ml). After 4 hr incubation, the supernatant was collected for measurement of IL-8 production using Duoset ELISA development kit (R&D systems, Minneapolis, Minn.). Compounds were added 2 hr before LPS stimulation.

Rhinovirus-Induced IL-8 and ICAM-1

Human rhinovirus RV16 (HRV) was obtained form American Type Culture Collection (Manassas, Va.). Viral stocks were generated by infecting Hela cells with HRV until 80% of the cells were cytopathic.

BEAS2B cells were infected with 5 MOI (multiplicity of infection of 5) of HRV and incubated for 2 hr at 33° C. with gentle shaking for absorption. The cells were then washed with PBS, fresh media added and the cells were incubated for a further 72 hr. The supernatant was collected for assay of IL-8 concentrations using Duoset ELISA development kit (R&D systems, Minneapolis, Minn.).

The level of ICAM-1 expressing cell surface was determined by cell-based ELISA. After appropriate incubation, cells were fixed with 4% formaldehyde in PBS. After quenching endogenous peroxidase by adding 0.1% sodium azide and 1% hydrogen peroxide, wells were washed with wash-buffer (0.05% Tween in PBS: PBS-Tween). After blocking well with 5% milk in PBS-Tween for 1 hr, the cells were incubated with anti-human ICAM-1 antibody in 5% BSA PBS-Tween (1:500) overnight. Wells were washed with PBS-Tween and incubated with the secondary antibody (HRP-conjugated anti-rabbit IgG, Dako Ltd.). The ICAM-1 signal was detected by adding substrate and reading at 450 nm with a reference wavelength of 655 nm using a spectrophotometer. The wells were then washed with PBS-Tween and total cell numbers in each well were determined by reading absorbance at 595 nm after Crystal Violet staining and elution by 1% SDS solution. The measured OD$_{450-655}$ readings were corrected for cell number by dividing with the OD$_{595}$ reading in each well. Compounds were added 2 hr before HRV infection and 2 hr after infection when non-infected HRV was washed out.

Rhinovirus-Titre Assay

MRC5 cells (human lung fibroblast, ATCC) were infected with 1 MOI (multiplicity of infection of 1.0) of HRV and incubated for 1 hr at 33° C. with gentle shaking for absorption. The cells were then washed with PBS, fresh media added and the cells were incubated for a further 96 hr. The supernatant was collected and 10-fold serial dilutions of virus containing supernatant were prepared. All titrations were performed by infecting confluent Hela cell monolayers with serially diluted supernatant ($10^{-1}$ to $10^{-5}$) and assessing cytopathetic effect by MTT assay 4 days after infection. The amount of virus required to infect 50% of Hela cells was calculated in each treatment as TCID$_{50}$ U/mL. Compounds were added 24 and 2 hr before HRV infection and 1 hr after infection when non-infected HRV was washed out.

LPS-Induced Neutrophils Accumulation in Mice

Non-fasted mice were dosed by the intra tracheal route with either vehicle, or the test substance at the indicated times (within the range 2-12 hr) before starting LPS treatment. At T=0, mice were placed into an exposure chamber and exposed to LPS. Eight hours after LPS challenge, animals were under anesthetized, the trachea cannulated and BALF extracted by infusing and withdrawing 1 ml of PBS into the lungs via a tracheal catheter. Total and differential white cell counts in the BALF samples were measured using a Neubaur haemocytometer. Cytospin smears of the BALF samples were prepared by centrifugation at 200 rpm for 5 min at room temperature and stained using a DiffQuik stain system (Dade Behring). Cells were counted using oil immersion microscopy. Treatment of mice with Compound (1) was found to inhibit neutrophil accumulation into the BALF when treated at 2, 8 or 12 hr before LPS challenge (Table 3 and 4)

TABLE 3

Effects of treatment with Compound (1)

| Treatment | Neutrophil numbers in BAL (×10⁵/mL) | |
|---|---|---|
| mg/ml Compound (1) | 2 hr pre-dose | 12 hr pre-dose |
| Vehicle | 20.2 ± 3.7 | — |
| 0.02 | 15.1 ± 2.1 | 20.1 ± 2.9 |
| 0.1 | 10.4 ± 1.6 | 16.7 ± 2.4 |
| 0.2 | 4.6 ± 1.2 | 14.3 ± 2.0 |

Results are presented as the mean ± SEM, n = 8

TABLE 4

Effects of treatment with Compound (1)

| Treatment | Neutrophil numbers in BAL (×10⁵/mL) 8 hr pre-dose |
|---|---|
| Vehicle | 16.38 ± 2.53 |
| Compound (1) 0.2 mg/ml | 9.65 ± 1.50 |

Results are presented as the mean ± SEM, n = 8

Allergen-Induced Eosinophil Accumulation in Guinea Pigs

Dunkin Hartley guinea pigs were immunized with ovalbumin. Six doses of vehicle or Example 8 (1.5 mg/ml) were administered by aerosol every 12 hours with the final dose being administered 2 hr before initiating of the allergen challenge (grade V, OVA; 10 µg/mL solution aerosolised using a De Vibliss ultrasonic nebuliser 2000, over a 30 min period). Two groups of animals received 6 doses of Example 8 whilst a further two groups received 6 doses of vehicle. 8 or 24 hours after OVA challenge (see group details above), the trachea was cannulated and BALF extracted. The procedure for this involved aspirating 5 ml of PBS into the lungs via a tracheal catheter. Total and differential white cell counts in the BAL fluid samples were measured using a Neubaur haemocytometer. Cytospin smears of the BAL fluid samples were prepared by centrifugation at 200 rpm for 5 min at room temperature and stained using a DiffQuik stain system (Dade Behring). Cells were counted blind using oil immersion microscopy.

Treatment of guinea pigs with Compound (1) was found to inhibit eosinophil accumulation into the BALF when investigated at 8 and 24 hr post ovalbumin challenge (Table 5)

TABLE 5

Inhibition of eosinophils in BALF following allergen challenge

| Treatment | Neutrophil numbers in BAL (×10⁵/mL) | |
|---|---|---|
| | 2 hr pre-dose | 12 hr pre-dose |
| Compound(1) | 12.4 ± 1.7 | 21.6 ± 3.9 |

Results are presented as the mean ± SEM, n = 6

Cigarette Smoke Model

A/J mice (males, 5 weeks old) were exposed to cigarette smoke (4% cigarette smoke, diluted with compressed air) for 30 min/day for 11 days using a Tobacco Smoke Inhalation Experiment System for small animals (Model SIS-CS; Sibata Scientific Technology, Tokyo, Japan). Test substances were given intra-nasally (35 µl of solution in 50% DMSO/PBS) and therapeutically twice daily for 3 days after the final cigarette smoke exposure. Twelve hours after the last dosing, animals were anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

The results of treatment with Compound (1) are shown in FIG. 1 (neutrophils) and FIG. 2 (activated alveolar macrophages). Data for cell numbers are shown as the mean±SEM. The cigarette smoke model used for this study is reported as a corticosteroid refractory system, (Medicherla S. et al., (2008); *J. Pharmacol. Exp. Ther.* 324(3):921-9) and it was confirmed that fluticasone propionate did not inhibit either neutrophil or macrophage accumulation into airways at 50 µg/mL (35 µl, bid, in), the same dose that produced >80% inhibition of LPS-induced neutrophil accumulation. However, treatment with Compound (1) was found to result in a marked, dose-dependent reduction in the numbers of both neutrophils and activated macrophages.

Ovalbumin Challenge/Parainfluenza Infection Model

Male Dunkin-Hartley guinea-pigs (300-350 g, n=6/group) were sensitised with 100 µg ovalubumin (OVA)+100 mg $Al_2(OH)_3$ in 1 ml normal saline (i.p.) on days 2 and 6. Parainfluenza virus (PIV-3; $10^6$ infectious units) or media without virus was nasally instilled on days 11 and 12. Animals were treated with either nebulised (i) fluticasone propionate at a dose of 1.5 mg per day (initial studies established that this dose of fluticasone propionate inhibited ovalbumin-mediated lung function changes in sensitized animals treated with PIV3 medium) or (ii) Compound (1) (0.15 mg per day) or (iii) a combination of fluticasone propionate and Compound (1) at the doses indicated above or (iv) the vehicle (DMSO:ethanol:saline, 30:30:40%) from days 10-15. All animals were challenged for 1 hr with nebulised OVA (10 µg/ml) on day 15 and repeated measurements of specific airways conductance ($sG_{aw}$) were made over a 24 h period using whole body plethysmography. Measurements of $sG_{aw}$ after OVA challenge are plotted as % change from baseline. FIG. 3 shows the effect of Compound 1 as monotherapy, while FIG. 4 shows its effects when administered in combination with fluticasone propionate. Treatment with Compound (1) alone was found to produce no effect on the initial ($1^{st}$ hr) bronchoconstrictor response to ovalbumin challenge, but markedly inhibited the subsequent response (2-12 hr post treatment). When co-administered with fluticasone propionate, both the initial and subsequent bronchoconstrictor responses evoked by ovalbumin challenge were inhibited.

Summary

The biological studies in vitro show that the compound of formula (1) is a potent inhibitor of p38 MAP kinase subtypes alpha and gamma with good efficacy in an in vitro model of anti-inflammatory activity (LPS-induced TNFα release from differentiated U937 cells and THP-1 cells). In addition, the compound of formula (1) shows the surprising properties of being able to inhibit both rhinovirus-induced inflammation and rhinovirus replication Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:
1. A compound of formula (1)

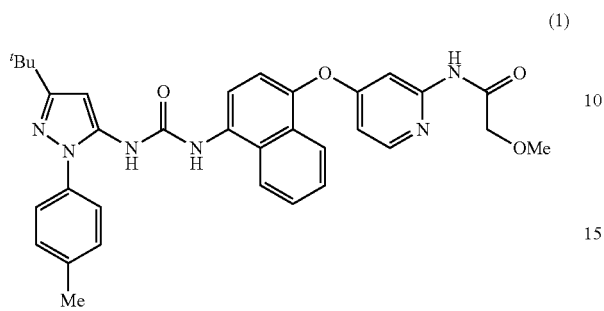

(1)

or a pharmaceutically acceptable salt thereof, including all stereoisomers and tautomers thereof.

2. A pharmaceutical composition comprising a compound according to claim 1, in combination with one or more pharmaceutically acceptable diluents or carriers.

3. A method of treatment of a condition selected from COPD, asthma, and pediatric asthma, which comprises administering to a subject in need thereof an effective amount of a compound of formula (I) according to claim 1.

4. A method of treatment of a condition selected from COPD, asthma, and pediatric asthma, which comprises administering to a subject in need thereof a pharmaceutical composition according to claim 2.

* * * * *